United States Patent
Rosen et al.

(10) Patent No.: US 10,792,126 B2
(45) Date of Patent: Oct. 6, 2020

(54) GUIDE FOR ZYGOMATIC DENTAL IMPLANT DRILLS

(71) Applicants: Dan Rosen, Encino, CA (US); Dennis G. Smiler, Sherman Oaks, CA (US)

(72) Inventors: Dan Rosen, Encino, CA (US); Dennis G. Smiler, Sherman Oaks, CA (US)

(*) Notice: Subject to any disclaimer, the term of this patent is extended or adjusted under 35 U.S.C. 154(b) by 178 days.

(21) Appl. No.: 15/984,341

(22) Filed: May 19, 2018

(65) Prior Publication Data
US 2019/0350674 A1 Nov. 21, 2019

(51) Int. Cl.
*A61C 1/08* (2006.01)

(52) U.S. Cl.
CPC ..................... *A61C 1/084* (2013.01)

(58) Field of Classification Search
CPC ....................................................... A61C 1/084
USPC .......................................................... 433/76
See application file for complete search history.

(56) References Cited

U.S. PATENT DOCUMENTS

| | | | | |
|---|---|---|---|---|
| 2,621,408 A * | 12/1952 | Hellmuth | ............... | A61C 1/082 433/76 |
| 2,675,615 A * | 4/1954 | Rosenberg | ............. | A61C 1/082 433/76 |
| 4,306,866 A * | 12/1981 | Weissman | ............... | A61C 1/082 433/215 |
| 5,741,133 A * | 4/1998 | Gordils | .................. | A61C 1/084 433/76 |
| 6,926,525 B1 * | 8/2005 | Rønvig | .................. | A61C 1/084 433/76 |
| 2009/0291414 A1 * | 11/2009 | Wang | ..................... | A61C 1/084 433/174 |

* cited by examiner

*Primary Examiner* — Sean M Michalski
*Assistant Examiner* — Mirayda A Aponte
(74) *Attorney, Agent, or Firm* — John Alumit

(57) ABSTRACT

An apparatus for guiding a zygomatic implant dental drill installed in a dental handpiece includes a collar configured to seat on a neck portion of the dental handpiece, with an offset post extending from the collar. A first extension extends from the offset post parallel to the neck portion, and a second extension extends from the first extension. The second extension is oriented parallel to the zygomatic implant dental drill, extending from the first extension to be co-terminal and off-set from the zygomatic implant dental drill. By observing the travel of the second extension along a patient's face, a dental surgeon can guide the zygomatic implant dental drill inside the patient toward the patient's zygomatic bone.

1 Claim, 6 Drawing Sheets

GUIDE FOR ZYGOMATIC DENTAL IMPLANT DRILLS

BACKGROUND

Dental implants are known in the art. Typical implants comprise a threaded artificial tooth root or fixture which is anchored (i.e., screwed into) the bone of a patient's upper or lower jaw. An extension piece, or abutment is anchored to the fixture, comprising a post extension upon which a crown is mounted, the crown comprising an artificial tooth. For effective fixation, the implant requires a sufficiently deep bone matrix in which to anchor. Often, a synthetic or organic bone graft material with osteogenic growth factors is used to replace missing bone.

In certain maxillary (i.e., upper jawbone) implant cases, there is insufficient bone for implant fixation, even with bone grafting. In such cases a zygomatic implant procedure is employed, where an elongated fixture is anchored at the implant site, through the maxilla, and upward at an angle into the zygomatic bone, which can support the implant and the forces brought to bear on it. The zygomatic implant procedure involves drilling tunnels in the zygomatic bones, and inserting metal implants into the tunnels. Thereafter, the abutment and crown may be installed according to convention. Due to the distance from the implant site on the maxilla to the anchoring site in the zygomatic bone, the zygomatic fixtures must be of greatly increased length, sometimes approaching 40, 50, or even 60 mm. Thus the drills used must be of equal length.

A problem exists in that the location of the zygomatic bone target site is very close to the floor of a patient's orbit, and the sensitive structures of the eye and its appendages contained therein. Since, barring pre-exposure of the infero-lateral orbital rim by an ophthalmologist, a dental surgeon cannot see the target site, its location must be estimated. Compounding this problem, due to the soft tissue and maxillary sinus between the point of entry and the zygomatic entry site, the zygomatic drill can change angle before reaching the zygomatic entry site. Furthermore, due to the length of the zygomatic drill, any slight deviation in the drill angle at the point of entry can result in a considerable deviation from the zygomatic entry site.

If the deviation results in entry of the drill (and fixture) into the patient's orbit, it can cause injury to lateral rectus and oblique muscles of the eye, among other structures, resulting in diplopia or more serious vision issues. For these reasons, there is a need for a guide that allows a dental surgeon performing a zygomatic implant procedure to know the precise location of a zygomatic drill as it travels from a patient's maxillary entry site to the zygomatic bone entry site, and adjust the angle of the zygomatic drill as necessary to avoid intrusion into the ocular cavity. There is also a need for a guide that performs these functions without the need for additional surgical intrusion into the patient. Additionally, there is a need for such a guide that avoids interfering with the zygomatic implant procedure while it is being carried out. These and other issues are addressed by the apparatus disclosed in the following summary, description, claims and drawings.

SUMMARY

In a primary embodiment an apparatus is provided for guiding a zygomatic implant dental drill installed in a dental handpiece, the dental drill having a tip, and the apparatus characterized by having a collar configured to seat on a neck portion of the dental handpiece. The neck portion is located adjacent a drill head of the dental handpiece and an offset post extends from the collar.

A first extension extending from the offset post in a direction substantially parallel to the neck portion, and a second extension extends from the first extension. The second extension is oriented parallel to the zygomatic implant dental drill, with the second extension extending from the first extension, such that it is co-terminal and off-set from the zygomatic implant dental drill. Due to that configuration, a user can detect the position of the zygomatic implant dental drill inside a patient by observing the position of the second extension as it travels outside the patient.

The neck portion of the dental handpiece preferably may have a reduced circumferential area along its length. In such an embodiment, the collar includes an opening configured to allow the reduced circumferential area to pass through the opening to disengage the apparatus from the dental handpiece. In an alternative embodiment, if the neck portion lacks a reduced circumferential area, the collar may have a hinged opening, allowing it to lock onto the neck portion and be removed. Additionally, either the neck portion, the collar, or both may include a registration point configured to engage the collar against the neck portion, such that rotational movement of the collar around the neck portion is arrested.

The offset post is preferably perpendicular to the collar and of sufficient length such that the first extension extends outside a patient's mouth sufficiently to allow the second extension to travel along the patient's face as the zygomatic implant dental drill travels through the patient toward the patient's zygomatic bone. Preferably, but not necessarily in this regard, the first extension may be substantially perpendicular to the offset post.

A first locking hinge may be provided between the first extension and the offset post, allowing the first extension and the offset post to be set in a plurality of positions relative to each other. Additionally, a second locking hinge may be provided between the second extension and the first extension, thus allowing the second extension to be set in a plurality of positions relative to each other. In various embodiments, the second extension may be marked with distance markings configured to match predetermined positions along the zygomatic implant dental drill in order to take measurements prior to, and during use, and the offset post may be a telescoping offset post, to account for differences in patient morphology, and ensure that the second extension can clear a patient's facial features when the zygomatic implant dental drill is in use.

The apparatus for guiding a zygomatic implant dental drill installed in a dental handpiece having a drill head, the dental drill having a tip, may also be characterized as comprising a collar configured to seat on the dental handpiece aft of the drill head and the zygomatic implant dental drill. This embodiment would be used in a case where the dental drill has is substantially linear, rather than having a neck portion and perpendicular head. In this embodiment, an offset post extends from the collar, and only a first extension extends from the offset post in a direction substantially parallel to the zygomatic implant dental drill.

In this embodiment, the first extension extends from the offset post such that it is co-terminal and off-set from the zygomatic implant dental drill, thereby allowing a user to detect the position of the zygomatic implant dental drill inside a patient by observing the first extension position outside the patient. Although the apparatus may be affixed to the dental handpiece by slipping it over the drill head, the dental handpiece may also have a reduced circumferential area along its length such that the collar is provided with an opening configured to allow the reduced circumferential area to pass therethrough. Such a configuration helps avoid contact with the zygomatic implant dental drill if the apparatus needs to be removed while the zygomatic implant dental drill is installed in the dental handpiece. Like the aforementioned embodiment, the dental handpiece may have a registration point configured to engage the collar, such that rotational movement of the collar around the dental handpiece is arrested.

In this second embodiment, the offset post extends substantially perpendicularly from the collar, and only the first extension extends substantially perpendicularly from the offset post. A locking hinge may be provided between the first extension and the offset post, with the locking hinge configured to lock in a plurality of positions. Similar to the aforementioned embodiment, the first extension is marked with distance markings configured to match predetermined positions along the zygomatic implant dental drill, and the offset post is a telescoping offset post.

In use, the apparatus provides a new method of operating a dental handpiece equipped with a zygomatic implant dental drill. The method principally comprises the steps of providing a guide having a collar, an offset post extending substantially perpendicularly from the collar, and a guide extension extending substantially perpendicularly from the offset post. The guide is configured such that the guide extension is substantially parallel to the zygomatic implant dental drill, and such that the guide extension extends as far as the zygomatic implant dental drill, while being parallel and offset from the zygomatic implant dental drill.

The dental surgeon locates a maxillary entry point for a zygomatic implant on a patient, and activates the dental handpiece, and inserting the zygomatic implant dental drill into the maxillary entry point. The surgeon then urges the zygomatic implant dental drill through the maxillary implant entry point and from the maxillary entry point toward the appropriate zygomatic bone of the patient. In the process, the surgeon observes the position of the guide extension as it travels outside the patient parallel to the zygomatic implant dental drill, and using the position of the guide to alter the course of the zygomatic implant drill, thereby avoiding damage to the patient. Once the zygomatic bone is reached, and sufficiently penetrated for anchoring the zygomatic implant base, the zygomatic implant dental drill is withdrawn from the patient.

Optionally, the method may include providing a locking hinge at a terminal end of the guide extension proximal the collar, and additionally, providing an offset extension between the offset post and the guide extension, the offset extension configured substantially perpendicular to both the offset post and the guide extension, for use in the instance of a dental handpiece having a neck portion and perpendicularly oriented drill head.

REFERENCE NUMBERS

The following reference numbers are used in the detailed description with reference to FIGS. 1-7:
  10. zygomatic implant
  12. conventional implant
  14. zygomatic fixture
  16. maxillary bone
  18. implant site
  20. zygomatic bone
  22. zygomatic drill
  24. maxillary sinus
  26. ocular orbit
  28. first embodiment dental handpiece
  30. drill head
  32. angled neck
  34. handle
  36. tip
  38. first embodiment zygomatic drill guide
  40. collar
  42. offset post
  44. first extension
  46. second extension
  48. opening
  50. registration point
  52. second embodiment dental handpiece
  54. second embodiment zygomatic drill guide
  56. second collar
  58. second opening
  60. second offset post
  62. single extension

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

Figure 1:
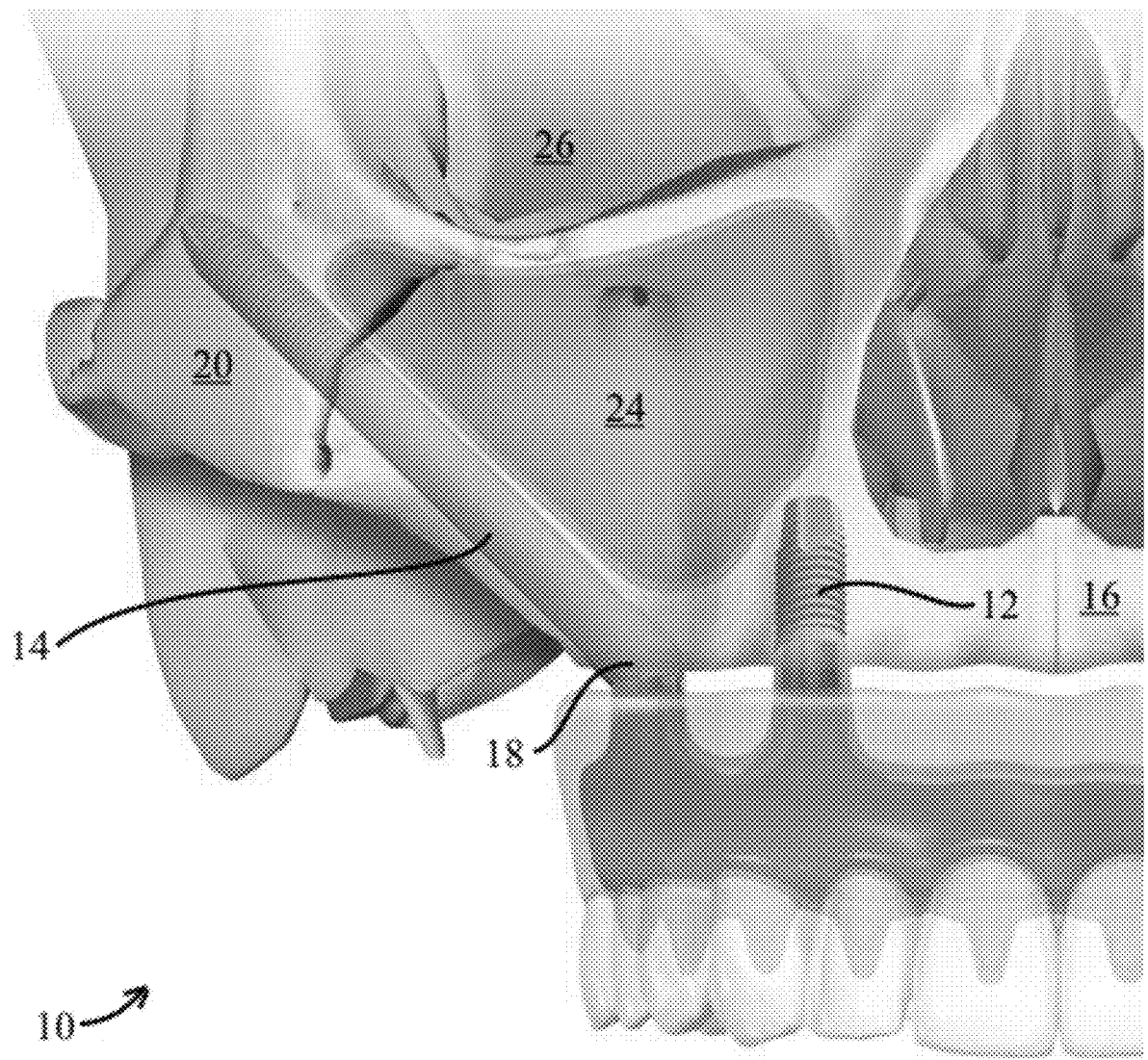
FIG. 1 illustrates a properly installed zygomatic dental implant, including a zygomatic fixture anchored in a patient's maxillary bone and zygomatic bone.

Referring to FIG. 1, a properly installed zygomatic implant 10 is shown. Adjacent a conventional implant 12. The zygomatic fixture 14 has been successfully mounted through the patient's maxillary bone 16 at an implant site 18, and terminating in the patient's zygomatic bone 20. As shown in this view, the zygomatic drill 22 (FIGS. 4-6) and following that, the zygomatic fixture 14 have traversed the space between the maxillary bone 16 and the zygomatic bone 20, and entered the zygomatic bone 20 without touching, occluding, or otherwise coming into contact with the patient's maxillary sinus 24 or ocular orbit 26, and the zygomatic fixture 14 is firmly embedded in the zygomatic bone 20. Due to the proximity of the maxillary sinus 24 and ocular orbit 26 to the trajectory of the zygomatic fixture 14 as it travels from the maxillary bone 16 to the zygomatic bone 20, any deviation from there is an elevated chance that the zygomatic drill 22 will create a path impinging on the ocular orbit 26 and/or maxillary sinus 24. Thus, when the zygomatic fixture 14 is installed, it can cause a variety of side effects.

Figure 2:
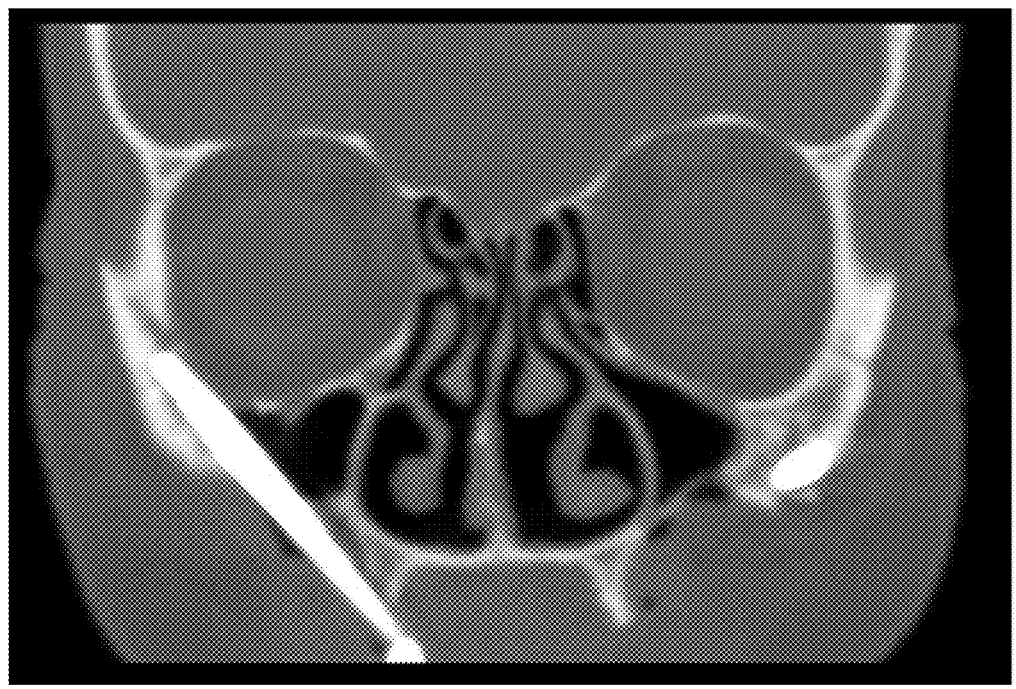
FIG. 2 illustrates an improperly installed zygomatic dental implant, wherein the zygomatic fixture has impinged on the patient's ocular orbit.

Referring to FIG. 2, an improperly installed zygomatic implant 10 is shown. In this case, the zygomatic fixture 14 has traversed the space between the maxillary bone 16 at the implant site 18 to the zygomatic bone 20, but due to the path of the zygomatic drill 22, the zygomatic fixture 14 has impacted the ocular orbit 26. In such a case, extraocular muscle damage frequently occurs, and the patient's vision can be severely impaired. Thus, ensuring that the zygomatic drill takes the proper path from the maxillary bone 16 to the zygomatic bone 20 is of paramount importance.

Figure 3:
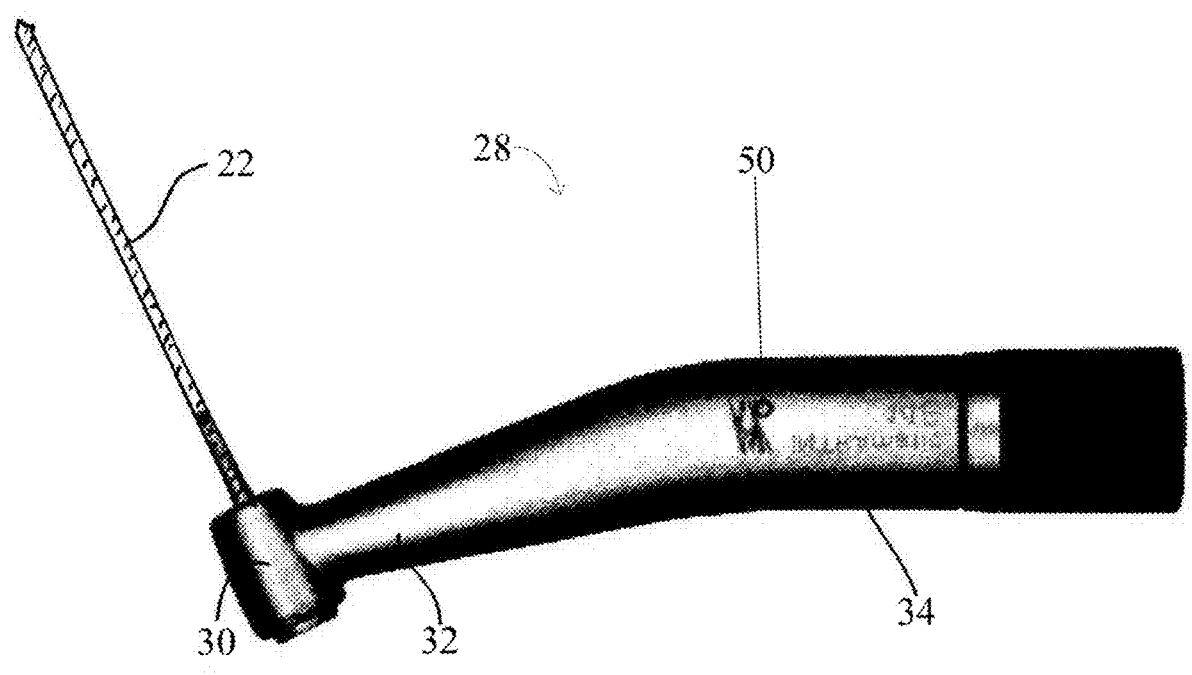
FIG. 3 illustrates a zygomatic drill installed on a first embodiment dental handpiece.

Referring to FIG. 3, in a primary embodiment, a zygomatic drill 22 is shown installed in a typical dental handpiece 28. The dental handpiece 28 includes a drill head 30 fixed to an angled neck 32 and a handle 34, which is connected to a pneumatic or similar powering apparatus (not shown). Because of the distance between the handle 34 where the dental handpiece 28 is held by a user, and the tip 36 of the zygomatic drill 22, it can be difficult to establish and maintain the proper angle as the zygomatic drill 22 enters the maxillary bone 16. Compounding this problem is the inability to detect precisely the location of the maxillary sinus 24 and ocular orbit 26 during drilling, and the difficulty in bracing a user's hand holding the dental handpiece 28 relative to the patient.

Figure 4:
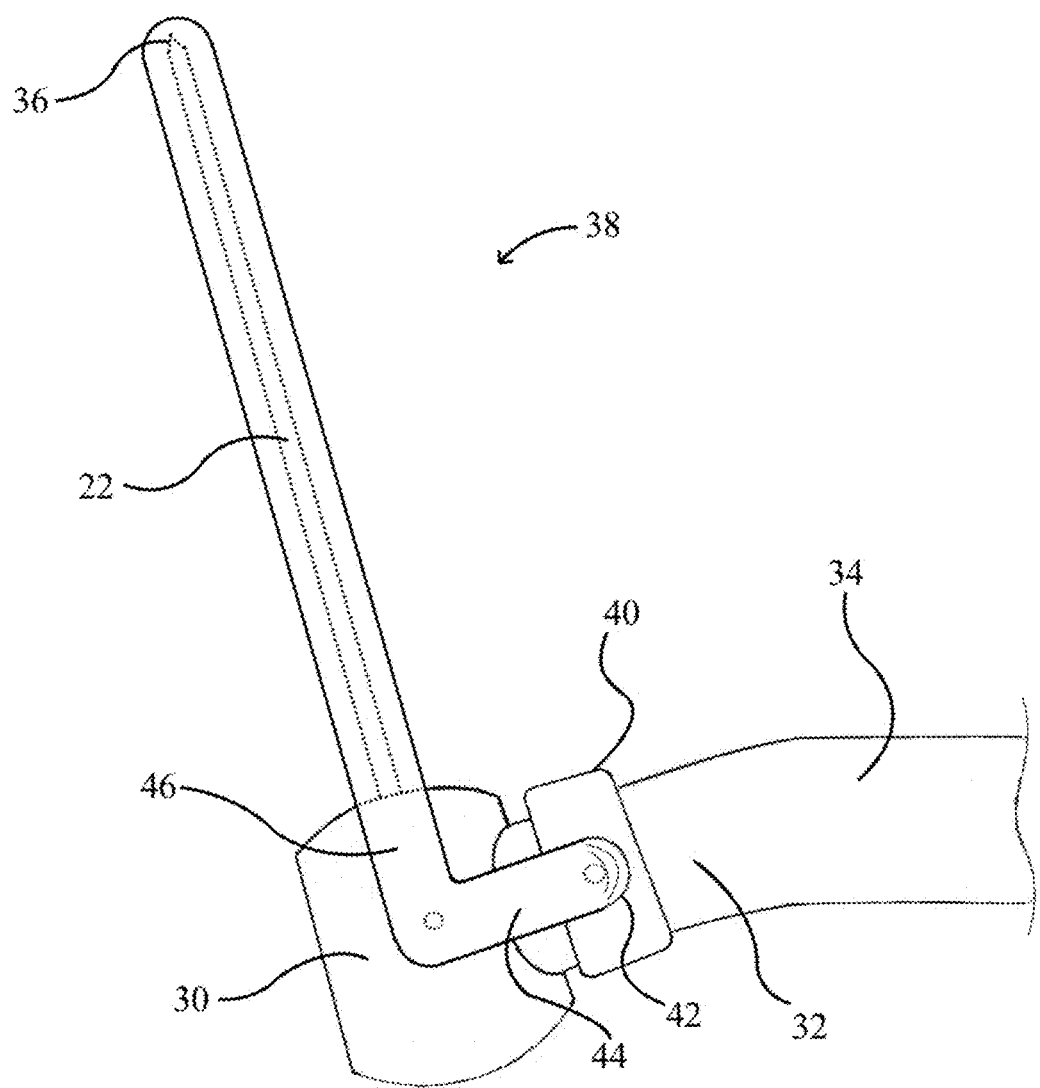
FIG. 4 illustrates a first side view of a first embodiment zygomatic guide installed on the first embodiment dental handpiece.

Referring to FIG. 4, a first embodiment zygomatic drill guide 38 is shown affixed to a dental handpiece 28 bearing a zygomatic drill 22. The zygomatic drill guide 38 includes a collar 40 for securely anchoring the zygomatic drill guide 38 to the angled neck 32 of the dental handpiece 28. The zygomatic drill guide 38 includes a collar 40 for seating on the angled neck 32 of the dental handpiece 28. An offset post 42 extends from the collar 40 laterally angled neck 32. The offset post A first extension 44 extends from the end of the offset post 42 to a position alongside the drill head 30, preferably centered such that the second extension 46 extends alongside the zygomatic drill 22 parallel, and entirely along its length to the tip 36.

Figure 5:
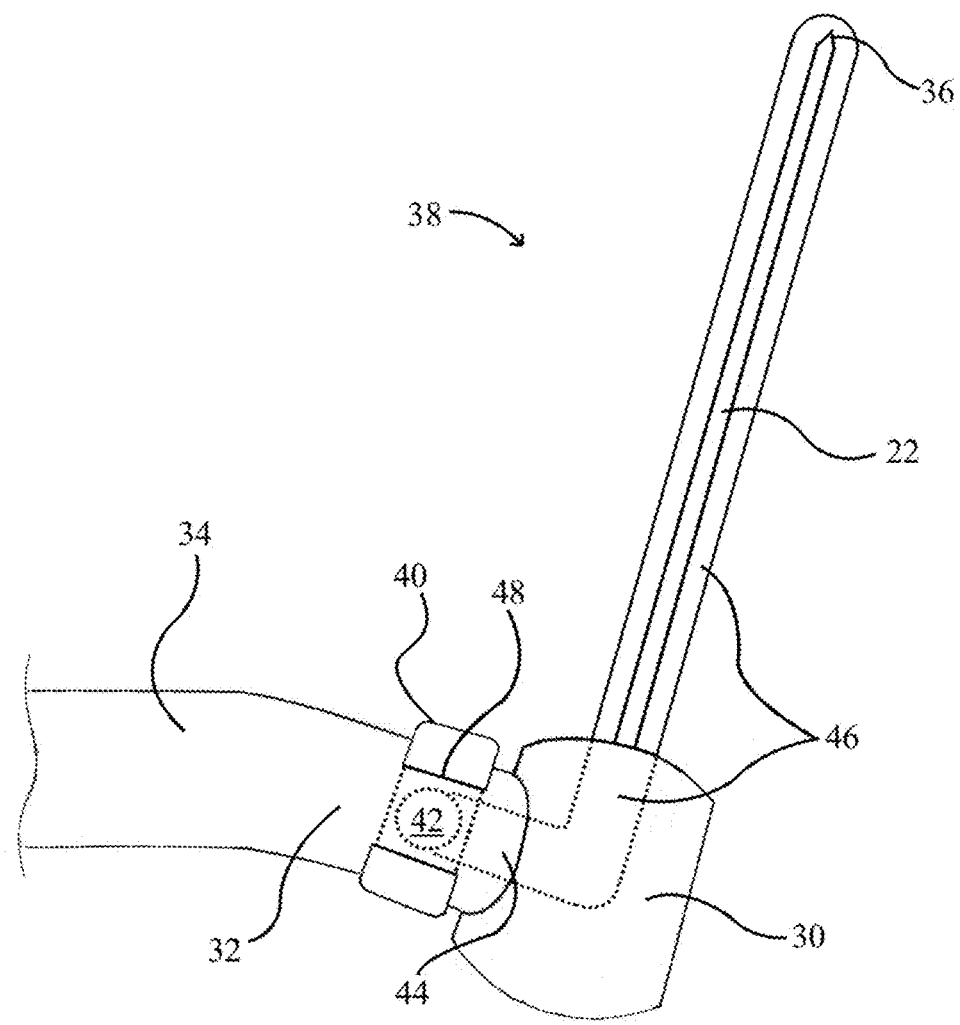
FIG. 5 illustrates a second side view of a first embodiment zygomatic drill installed on the first embodiment dental handpiece.

Referring to FIG. 5, the collar 40 preferably includes an opening 48 opposite the offset post 42, thus enabling the zygomatic drill guide 38 to be easily installed on, and removed from the dental handpiece 28.

With the second extension 46 in a fixed position relative to the zygomatic drill 22, the zygomatic drill 22 can be activated and urged through the maxillary bone 16 at an implant site 18, and the operator can follow the path of the second extension 46 along the outside of a patient's face (not shown) to ensure that the zygomatic drill 22 continues in an accurate path toward and into the zygomatic bone 20, without impacting the ocular orbit 26 or other structures where it may cause harm.

Figure 6:
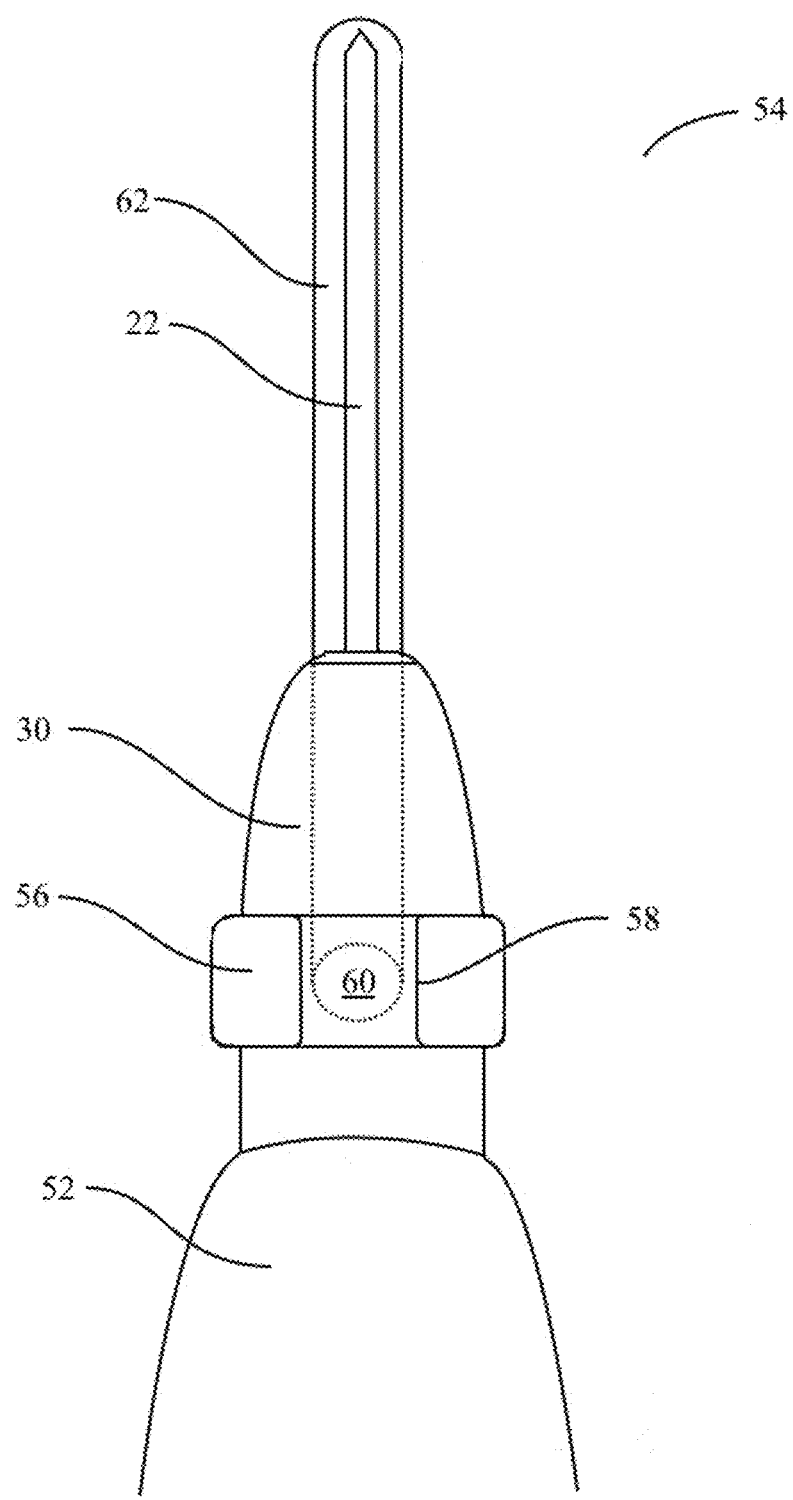
FIG. 6 illustrates a second embodiment zygomatic guide installed on the second embodiment dental handpiece.
Figure 7:
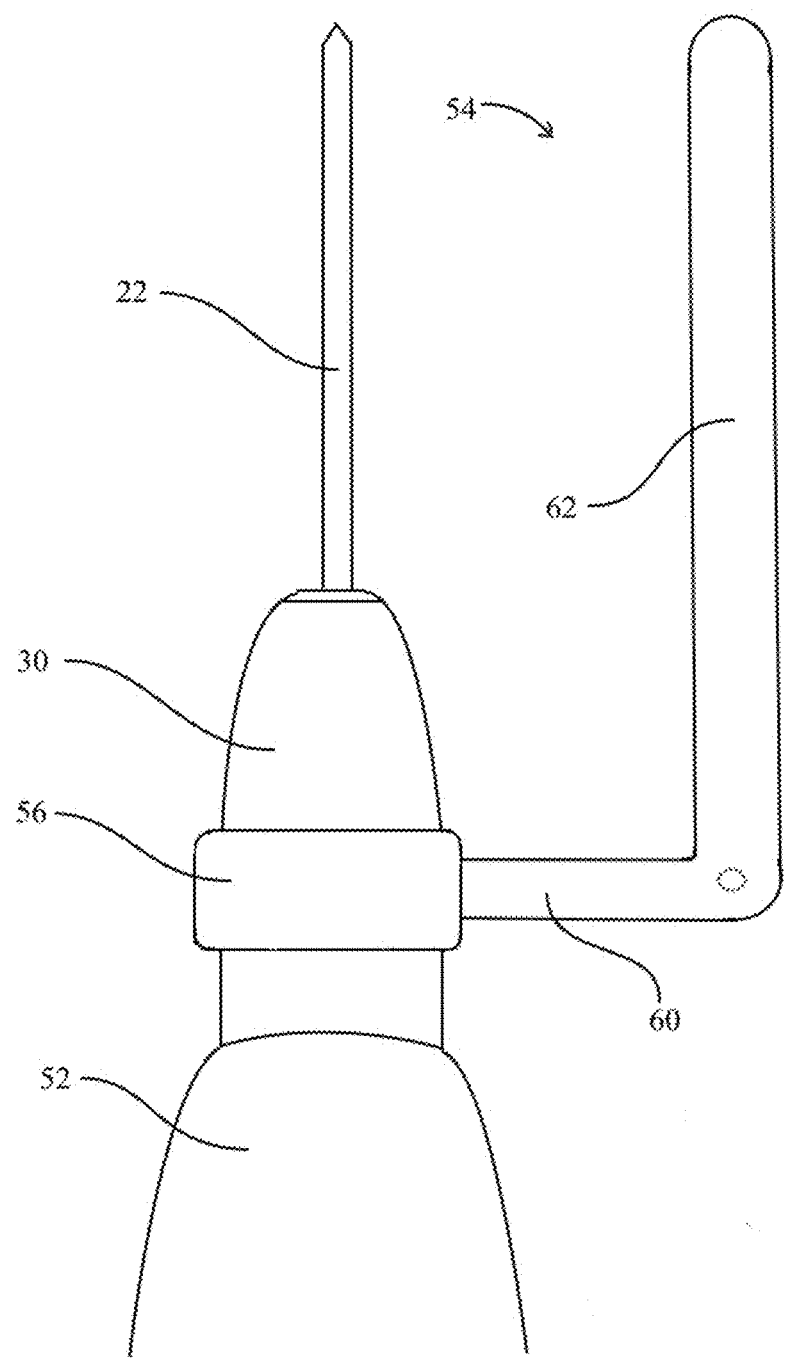
FIG. 7 illustrates the second embodiment zygomatic guide showing a single extension extending from a second offset post.

Referring to FIGS. 6 and 7, a second embodiment dental handpiece 52 is shown. In this embodiment, the handpiece is substantially linear or pen-shaped, and lacks an angled neck 32 (FIGS. 4 and 5). Rather, the drill head 30 occupies a position at the terminal end of the dental handpiece 52. The zygomatic drill 22 is affixed to the head in substantially the same manner as the first embodiment dental handpiece 28. Instead of affixing to the angled neck 32, the second embodiment zygomatic drill guide 54 affixes to the second embodiment dental handpiece 52 at a position on or just below the drill head 30.

The second embodiment zygomatic drill guide 54 is similar to the first embodiment zygomatic drill guide 28 in that it includes a second collar 56, preferably with a second opening and a second offset post 60. However, since the second collar 56 is located immediately below the zygomatic drill 22, centered on the drill head 30, there is no need for a second extension 46 (FIGS. 4-5). Rather, a single extension 62 is provided, rising the height of the zygomatic drill 22. As shown in FIG. 6, due to the length of the second offset post 60, the single extension 62 can travel along a patient's face as the zygomatic drill 22 enters the maxillary bone 16 at the implant site 18, and travels to the zygomatic bone 20. As shown in FIG. 7, like the first embodiment zygomatic drill guide 38, the single extension 62 of the second embodiment zygomatic drill guide 54 is co-linear with the zygomatic drill 22, enabling a user to accurately gauge the zygomatic drill's position as it travels through a patient's maxillary bone 16 to the zytomatic bone 20 without affecting the ocular orbit 26 or other sensitive structures.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A method of operating a dental handpiece equipped with a zygomatic implant dental drill, the method comprising the steps of:
   providing a guide having a collar, an offset post extending perpendicularly from the collar, and a guide extension extending perpendicularly from the offset post;
   configuring the collar such that the collar at least partially surrounds the dental handpiece, with the offset post extending away from the collar, a first extension oriented perpendicular to the offset post, and the guide extension oriented perpendicular to the first extension, such that the guide extension is parallel to the zygomatic implant dental drill;
   configuring the guide extension such that the guide extension extends as far as the zygomatic implant dental drill, while being parallel and offset from the zygomatic implant dental drill;
   locating a maxillary entry point for a zygomatic implant on a patient;
   activating the dental handpiece, and inserting the zygomatic implant dental drill into the maxillary entry point;
   urging the zygomatic implant dental drill from the maxillary implant entry point toward a zygomatic bone of the patient;
   observing the position of the guide extension on the outside of the patient as it travels parallel to the zygomatic implant dental drill, and using the position of the guide extension to confirm the course of the zygomatic implant drill avoids damage to the patient; and withdrawing the zygomatic implant dental drill from the patient once the zygomatic implant dental drill enters the zygomatic bone.

* * * * *